United States Patent

Devaraj et al.

[11] Patent Number: 5,818,587
[45] Date of Patent: Oct. 6, 1998

[54] IMAGE MEASURING APPARATUS

[75] Inventors: Balasigamani Devaraj; Masaki Kobayashi; Motohiro Takeda, all of Yamagata; Masashi Usa, Sendai; Hiroshi Ishihata, Sendai; Hiroshi Horiuchi, Sendai; Humio Inaba, Sendai, all of Japan

[73] Assignee: Biophotonics Information Laboratories Ltd., Yamagata, Japan

[21] Appl. No.: 645,967

[22] Filed: May 10, 1996

[30] Foreign Application Priority Data

Nov. 16, 1995 [JP] Japan ................................. 7-298447

[51] Int. Cl.[6] ........................................................ G01B 9/02
[52] U.S. Cl. ............................................. 356/349; 356/345
[58] Field of Search ................................. 356/318, 419, 356/446, 345, 349, 432–433

[56] References Cited

U.S. PATENT DOCUMENTS

| 4,468,197 | 8/1984 | Provost ........................ 433/30 |
| 4,836,206 | 6/1989 | Maxwell et al. ............... 356/419 |
| 5,570,182 | 10/1996 | Nathel et al. ................. 356/345 |

FOREIGN PATENT DOCUMENTS

| 2-150747 | 6/1990 | Japan . |
| 3-11346 | 1/1991 | Japan . |
| 3-11737 | 1/1997 | Japan . |

Primary Examiner—Frank G. Font
Assistant Examiner—Jason D. Vierra-Eisenberg
Attorney, Agent, or Firm—Staas & Halsey

[57] ABSTRACT

An image measuring apparatus for measuring an image of a tooth or gum applies the radiation of a laser beam to permit extremely quick, reliable, safe detection of dental caries and other dental pathological conditions. The low incident power of the laser radiation would not cause damage or pain to the tissue, such as the tooth or gum. The image measuring apparatus is equipped with a light source which emits light having at least a wavelength in a range of 500 nm or more to less than 600 nm; it uses the light emitted from the light source to obtain 2-dimensional images or computed tomographic images of a tooth or gum from the light, which has been transmitted through the tooth or gum, by using an optical heterodyne detection method.

11 Claims, 7 Drawing Sheets

IMAGE MEASURING APPARATUS

BACKGROUND OF THE INVENTION

1. Field of the Invention

The present invention relates to an imaging apparatus to obtain images of the internal structure of human teeth or gums and use the obtained images for diagnosis in dentistry.

2. Description of the Related Art

The detection or diagnosis of a decayed tooth is most important and essential in odontotherapy. Hitherto, radiographic diagnoses have generally been carried out.

There is a danger, however, that X-rays adversely affect biomedical tissues and the requirements in carrying out radiographic diagnoses are becoming more strict to ensure safety. Besides, it is difficult to detect primary caries even by radiographic inspection.

Radiography, which is based on two-dimensional transmitted images, is incapable of providing high resolution. As a matter of fact, dental caries which can be detected by radiography is in its end stage; therefore, radiography is not suited for the early detection of dental caries.

In addition, tomographic image measurement by radiographic scanning in an oral cavity is generally avoided due to higher power requirements and longer exposure times of the ionizing X-rays radiation to the oral cavity that could result in radiation injury; therefore, it is unlikely to obtain a radiographic CT image of a tooth in the oral cavity.

SUMMARY OF THE INVENTION

The present invention would permit computed tomographic imaging of human teeth and gums and would also provide an image measuring apparatus that uses a laser source and permits extremely quick, painless, reliable and safe detection of dental caries.

The difference in the optical properties of carious dentin and healthy dentin would be utilized for caries diagnosis.

To this end, according to the present invention, there is provided an image measuring apparatus which is equipped with a light source for emitting light of a predetermined wavelength and which produces an image of a tooth or gum based on transmitted light according to the optical heterodyne detection method.

Preferably, the aforesaid light source emits light at least at one wavelength in the range from 500 nm or more to less than 600 nm. It is further preferable that the light source emit light at least at one wavelength in the range from 500 nm or more to less than 560 nm. Specifically, an argon ion laser which emits light at the wavelength of 514.5 nm or the second harmonics of an Nd:YAG laser which emits light at the wavelength of 532 nm.

In another preferred form, a second light source which emits light at least at one wavelength in the range from 600 nm or more to less than 1300 nm is provided in addition to the aforesaid light source, and it is switched over from the first light source.

Since the image measuring apparatus according to the present invention is intended for the measurement of teeth or gums, it is preferable that the apparatus be provided with a first optical fiber for transmitting the light emitted from the light source into an oral cavity and a second optical fiber for collecting the transmitted light, that is, the light which has passed through the tooth or gum, out of the oral cavity.

Alternatively, the image measuring apparatus may be equipped with the first optical fiber for transmitting the light emitted from the light source and the second optical fiber for receiving the transmitted light which has passed through the tooth or gum, out of the oral cavity, wherein either the emitting end of the first optical fiber or the receiving end of the second optical fiber is placed in the oral cavity and the other is placed out of the oral cavity.

The highly scattering nature of a biological tissue poses a serious problem when attempting to obtain a two-dimensional image or CT image by employing the transmitted light that has passed through the tooth or gum. To successfully reconstruct the two-dimensional image or CT image algorithm according to the conventional projection slice or filtered back projection method, it is required to accurately detect the least deviated forward scattered optical component that apparently propagates along the optical axis.

The optical heterodyne detection method, which provides high directionality high selectivity and high detection sensitivity, is best suited for the purpose described above, when compared to other optical detection methods.

In the optical heterodyne detection method, the heterodyne detection efficiency significantly drops if the wave fronts and the plane of polarizations of the signal and a pre-determined reference beams that are superimposed on each other fail to coincide. Hence, the system is provided with high directionality which enables to select only the apparent straight forward transmitted optical component.

The attempt to successfully apply the optical heterodyne detection method to an optical CT apparatus for a biomedical specimen has been disclosed in Japanese Patents Laid-Open Nos. 2-110345, 2-11346, 2-150747, and 3-111737.

Figure 1:
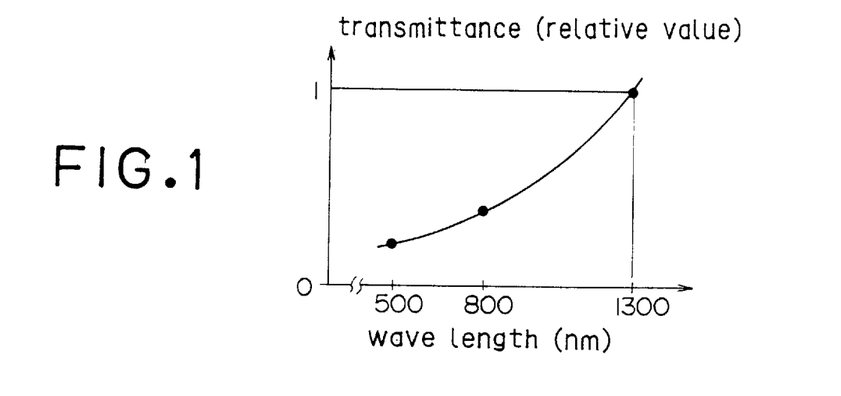
FIG. 1 is a graph showing the transmittance of light through a biological tissue at different wavelengths.
Figure 2:
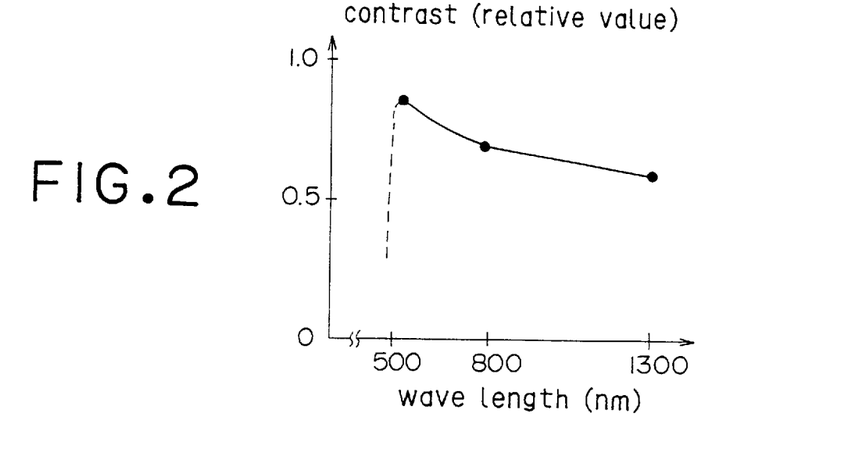
FIG. 2 is a graph showing the contrast obtained when measuring images of teeth and gums by using light of various wavelengths.

FIG. 1 is a graph showing the transmittance of light passing through an organism; FIG. 2 is a graph showing the contrast between light beams of different wavelengths used to measure the images of teeth and gums.

As can be seen from the graph in FIG. 1, the infrared radiations exhibit better transmittance of light beams through biological tissue. Optical methods currently in use for biomedical imaging use light in the wavelength range from 600 nm to 1300 nm known as "the therapeutic window of an organism" as light in this wavelength range has higher penetration into the tissues. Hence, therefore, light in the wavelength range from 600 nm to 1300 nm has been commonly used for that purpose.

The results of the research on teeth and gums conducted by the inventor have revealed, however, that the light in the wavelength range from 500 nm to 600 nm, especially from 500 nm to 560 nm, which is known as the wavelength range of green, is ideally suited for teeth or gums in respect of the image contrast as shown in FIG. 2. The green light however exhibits lower transmittance as shown in FIG. 1. This means that higher incident power of light is required, but it is still preferable to use the light in the green wavelength range for measuring the image of a tooth or gum because of the better image contrast.

The inventor has also used light at the wavelength of 488 nm, but found that the transmitted light was too low to detect and reconstruct a meaningful image.

Figure 3:
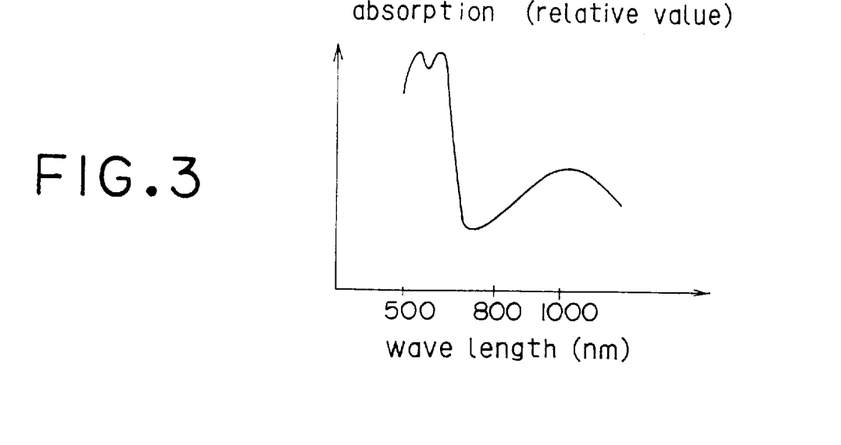
FIG. 3 is a graph showing the absorption of light by the hemoglobin of blood at different wavelengths.

FIG. 3 is a graph showing the absorption of light by blood hemoglobin in relation to different wavelengths of light. The blood flows through teeth and gums and the hemoglobin in the blood stream is known to absorb less light in the range of 650 nm to 1300 nm (hereinafter referred to as "near infrared range") as shown in FIG. 3. Hence, if the light in the near infrared range is used, then an image which carries a different type of information from that of the image obtained using the light in the green wavelength range can be obtained. Accordingly, providing the system with the first light source for emitting light in the green wavelength range and the second light source for emitting light in the near infrared range makes it possible to compare the images obtained using the two light sources so as to obtain more information on teeth or gums.

DESCRIPTION OF THE PREFERRED EMBODIMENTS

The embodiments of the present invention will now be described.

Figure 4:
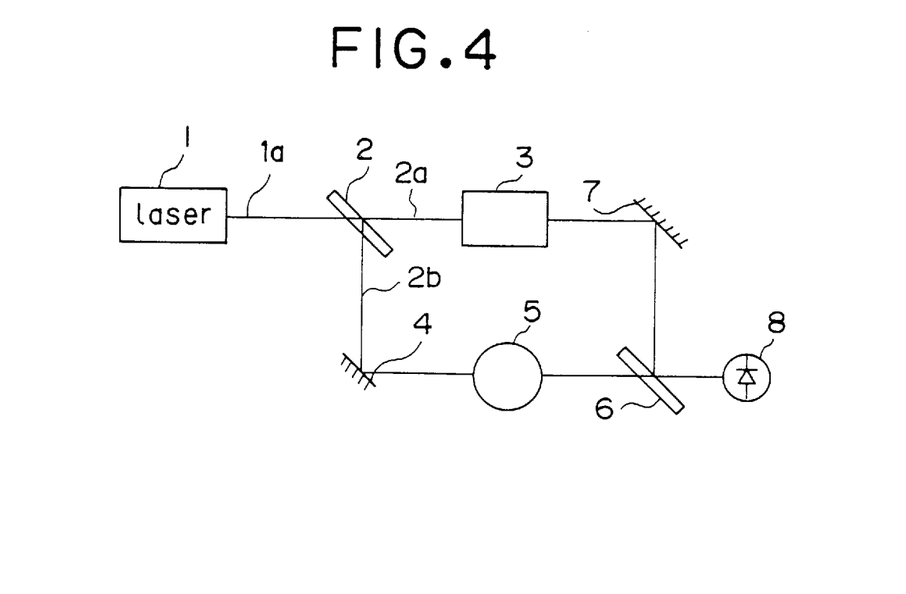
FIG. 4 is a schematic diagram showing an example of the optical heterodyne detection method.

FIG. 4 is a schematic diagram showing an example of the optical heterodyne detection method.

In the optical heterodyne detection method, a light source 1 which has a long coherence length, is used; the laser beam 1a is split by a first beam splitter 2 in a system configured as a Mach-Zehnder interferometer as shown in FIG. 4, for example. The first optical path 2a is equipped with an optical device 3 such as an accousto-optical modulator (AOM) for shifting the frequency of the laser beam 1a to provide a reference beam. In the second optical path 2b, a sample 5 is placed in a position after the light beam is reflected by a mirror 4 in this embodiment; the light which has passed through the sample 5 serves as a signal beam. On a second beam splitter 6, the signal beam which has passed through the sample 5 is precisely mixed with the reference beam which has been frequency-shifted by the optical device 3 and reflected by a mirror 7 in such a manner that the optical axes of these two beams exactly coincide.

The interference resulting from the optical mixing, i.e. superimposition, enables an optical detector 8 to detect an electrical signal, namely, an IF signal, which corresponds to a frequency based on the difference between the frequency of the signal optical beam and the reference beam.

The present invention provides a useful apparatus for diagnoses by applying the optical heterodyne detection method to obtain two-dimensional transmitted images of teeth and further to the measurement of optical CT images of the teeth and gums.

Figure 5:
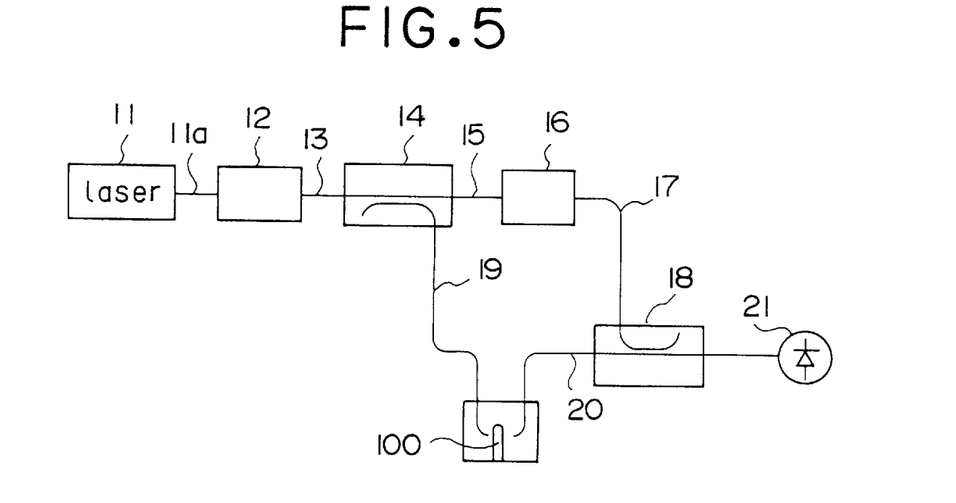
FIG. 5 is a block diagram showing an example of an image measuring apparatus wherein the optical heterodyne detection method shown in FIG. 4 has been applied to the image measurement of teeth or gums.

To apply the optical heterodyne detection method to a narrow space in a human oral cavity, an optical fiber as shown in FIG. 5 is preferable to a free-space propagation system based on the propagation of laser beams in free-space.

A laser beam 11a emitted from a laser 11 is coupled to a fiber 13 via an optical system 12. A fiber coupler 14 serves as the optical device which corresponds to the beam splitter 2 in FIG. 4; one of the two split beams is frequency-shifted by a frequency shifter 16 via an optical fiber 15 to provide a reference beam which goes to a second optical fiber coupler 18 via an optical fiber 17; the other beam is transmitted into an oral cavity through a flexible optical fiber 19 and it is incident on an object to be measured (a tooth 100). The transmitted light after passing through the object to be measured, namely, the tooth 100, is taken back out of the oral cavity through an optical fiber 20 to provide a signal beam. The signal beam is mixed with the reference beam by the second optical fiber coupler 18. As a result, an electrical signal, namely, an IF signal, is detected with high sensitivity through an optical detector 21.

Figure 6:
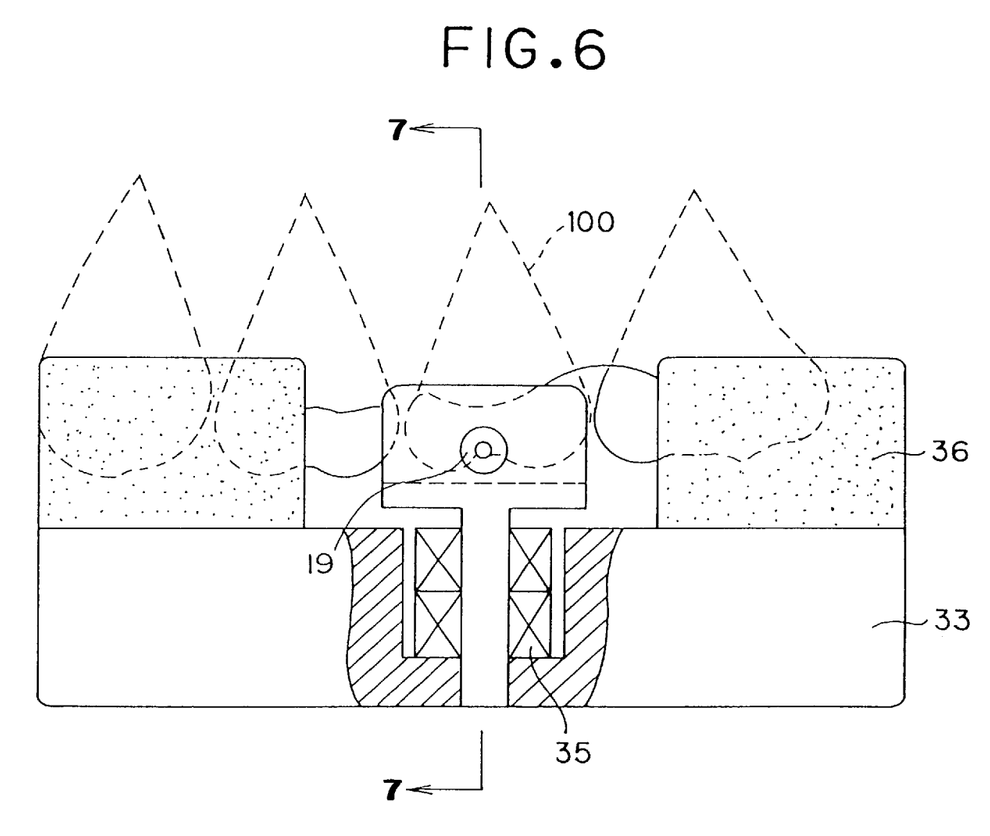
FIG. 6 is a side view showing a basic structure of a section, namely, a measuring head assembly, for radiating a light beam to a tooth or gum in an oral cavity and for collecting the transmitted light via the image measuring apparatus shown in FIG. 2.
Figure 7:
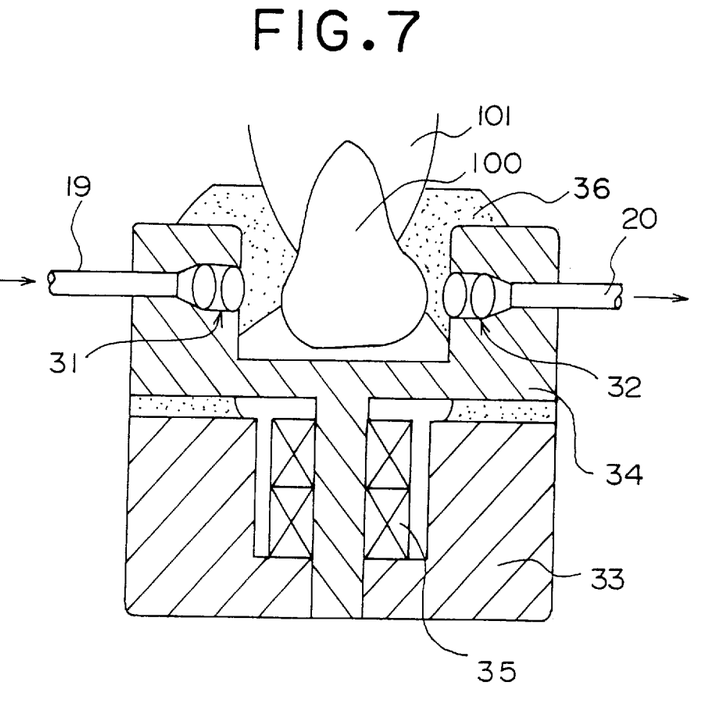
FIG. 7 is a cross-sectional view taken along arrows 7—7 of FIG. 6.

FIG. 6 is a side view and FIG. 7 is a cross-sectional view taken along arrows 7—7 of FIG. 6, both showing a basic structure of the section, namely, a measuring head assembly, for illuminating a tooth or gum in an oral cavity and for collecting the transmitted light in the image measuring apparatus shown in FIG. 2.

The single optical fiber 19 is led into an oral cavity and collected and directed by an optical system 31 to objects to be measured, namely, the tooth 100 and gum 101. The transmitted light is carried out of the oral cavity through the optical fiber 20 via a matching optical system 32 which is placed on the opposite side of the emitting optical system 31 and which is similar to the emitting optical system 31. The optical systems 31, 32 which are located at the ends of the optical fibers 19, 20, are made of rod lens systems or microlens systems. The optical fibers 19, 20 are retained by a fiber holder 34 which is movable with respect to a substrate 33. The substrate 33 is fixed by a fixing component 36 in the oral cavity in such a manner that the fixing component 36 clamps a tooth or gum in the vicinity of the tooth or gum to be measured.

The fiber holder 34 can be given an extremely small turn with respect to the substrate 33 by a micromotor 35. Providing a parallel moving means (not shown) for moving the paired fibers 19 and 20 on the fiber holder 34 when the fiber holder 34 is in a certain angle makes it possible to obtain the transmittance data required for producing a CT image by an optical heterodyne detection system.

Figure 8:
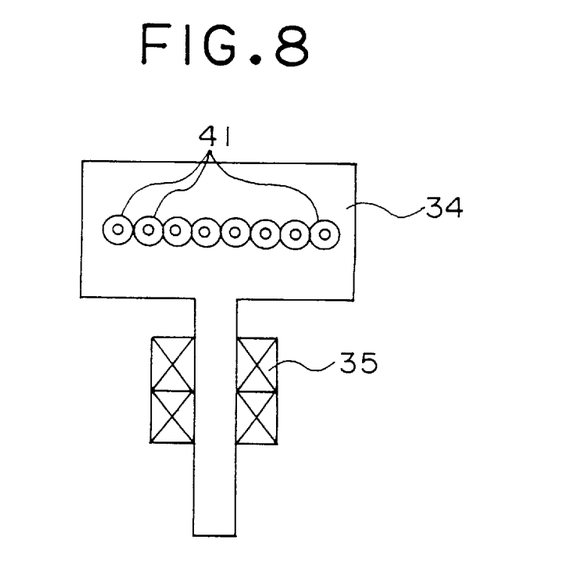
FIG. 8 is a schematic diagram showing of a fiber holder shown in FIGS. 6 and 7.
Figure 9:
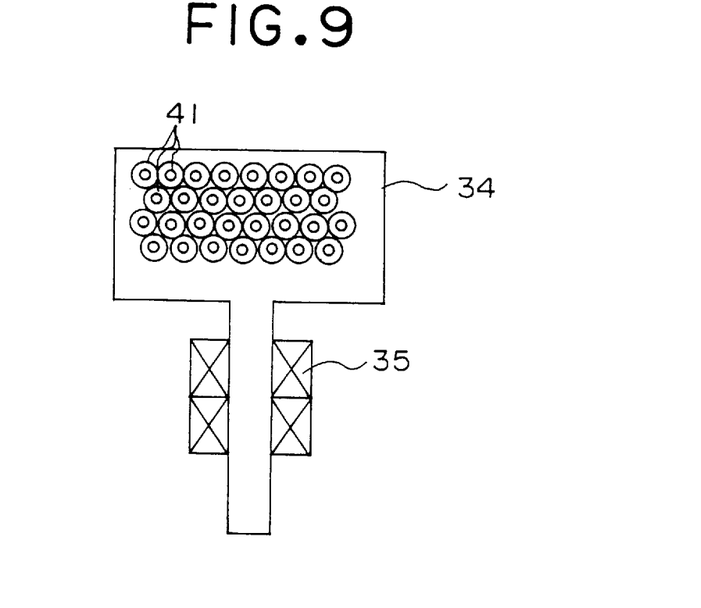
FIG. 9 is a schematic diagram which also corresponds to a fiber holder shown in FIGS. 6 and 7.

FIGS. 8 and 9 are schematic diagrams showing the components constituting the fiber holder shown in FIGS. 6 and 7. An array of paired fibers are attached to the fiber holder rather than just a single pair of fibers.

FIG. 8 shows a 1-dimensional array of aligned fibers 41; FIG. 9 shows a 2-D array of fibers 41 which are arranged in a fiber bundle.

Specifically, in FIG. 8, eight pairs of fibers are arranged in a 1-D array, whereas in FIG. 9, thirty pairs of fibers are arranged in a 2-D array. This means that eight and thirty pieces, respectively, of transmittance data can be obtained for every angle. This eliminates the need for moving the paired fibers in parallel on the fiber holder 34 which has been described in reference to FIGS. 6 and 7, and the speed for acquiring the data required for producing a CT image will be increased 8-fold and 30-fold, respectively.

Figure 10:
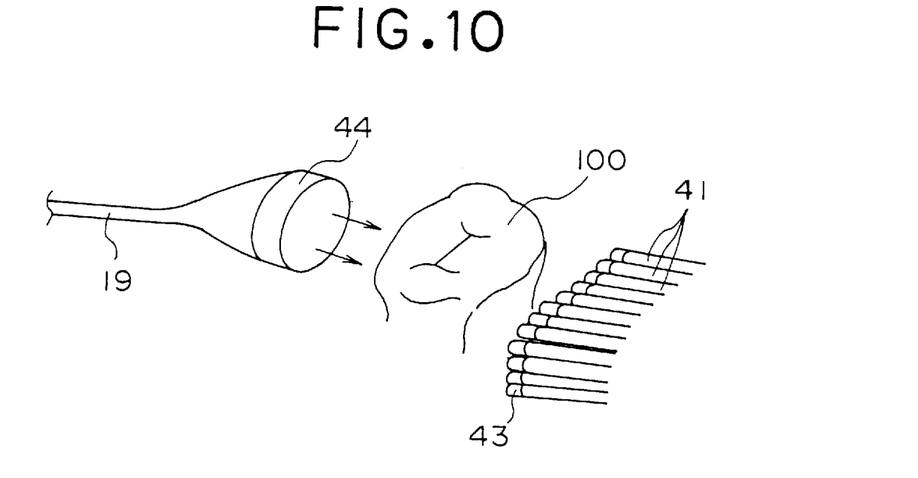
FIG. 10 is a conceptual diagram showing a system wherein the radiating side of the thirty pairs of associated fibers of FIG. 9 form a single parallel light beam; a fiber bundle consisting of thirty optical fibers shown in FIG. 9 is used.

In a conceptual diagram given in FIG. 10, the incident side of the thirty pairs of fibers form a single parallel beam and the fiber bundle comprised of the thirty optical fibers 41 shown in FIG. 9 receives the transmitted light. This is advantageous in that the optical system can be simplified.

In FIG. 10, a laser beam propagating through the optical fiber 19 is expanded by an optical system 44 before it is incident on the object to be imaged such as the tooth 100. The transmitted light is admitted to a receiving optical fiber 42 via an optical system 43 and mixed with the reference before it is passed on to a signal processing system.

Figure 11:
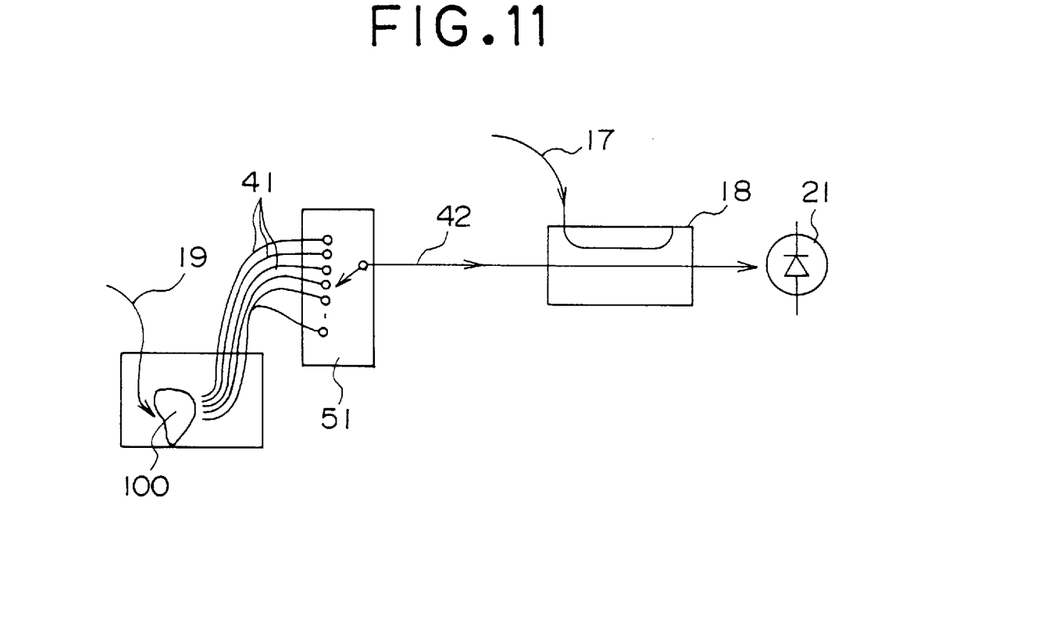
FIG. 11 is a schematic diagram showing a system for processing the transmitted light which has entered the optical fibers.
Figure 12:
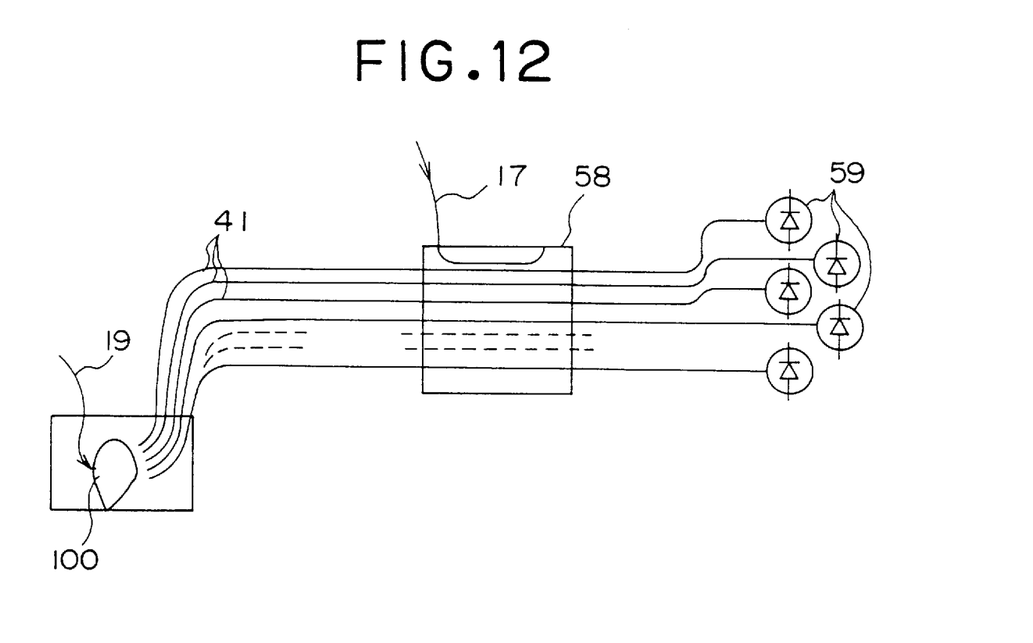
FIG. 12 is a schematic diagram showing a system for processing the transmitted light which has entered the optical fibers.

As illustrated in FIG. 11, the transmitted optical signals are collected by an array and the optical fibers array 41 shown in FIG. 8 through FIG. 10 are fed to the optical fiber 42 through sequential switching performed by an optical switch 51 in the optical fiber system, then they are led into the fiber coupler 18. The IF signals are sequentially generated due to the mixing of the signal from a single fiber of the bundle 41 and a single reference in the fiber coupler 18. The IF signal is then passed on to an optical detector 21 one after another, corresponding to the respective signal beams which have been mixed with the reference beams transmitted through the optical fiber 17 and which have been received by the optical detector 21. Further, as shown in FIG. 12, simultaneous signal detection may be carried out by an array of fiber couplers 18 and a detector array of 59 so as to increase the signal processing speed, thereby achieving high-speed acquisition of CT images.

FIGS. 6 and FIG. 7 show the method for fixing the

FIGS. 6 and FIG. 7 show the method for fixing the

Figure 13:
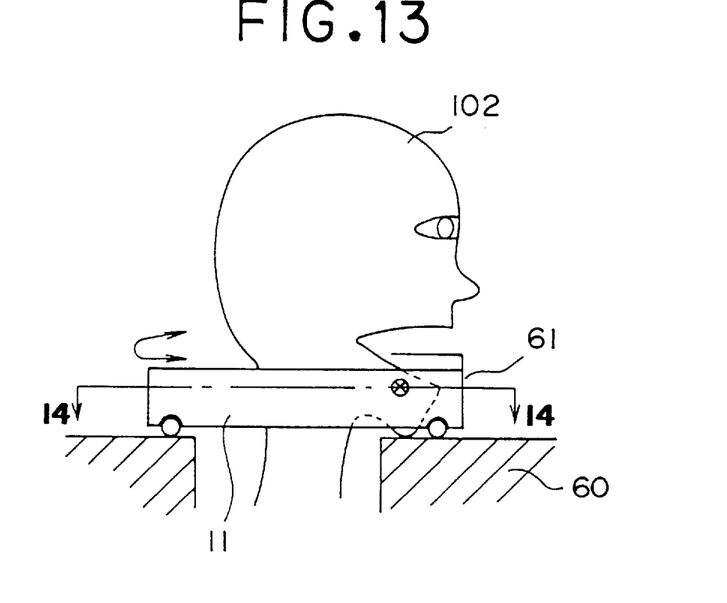
FIG. 13 is a schematic diagram showing another example of the measuring head assembly in the image measuring apparatus shown in FIG. 2.
Figure 14:
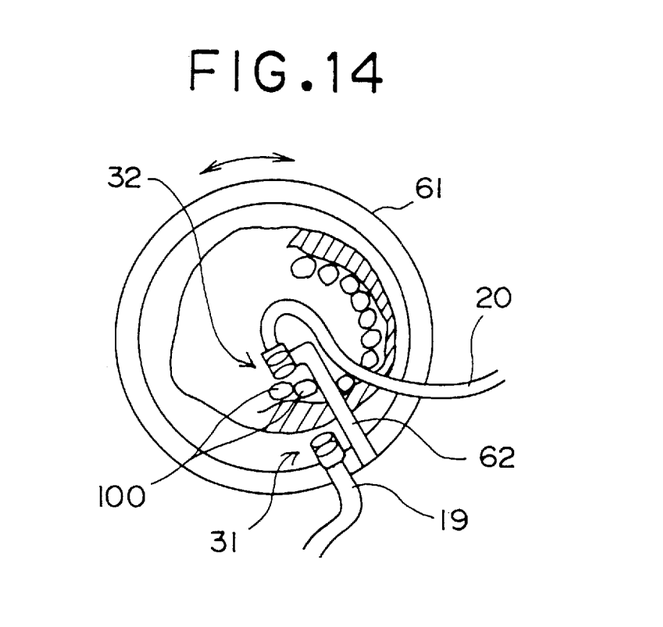
FIG. 14 is a cross-sectional view taken along 14—14 shown in FIG. 13.

FIGS. 6 and 7 show the method for fixing the measuring system, which has a rotating section, in the oral cavity. FIGS. 13 and 14 are conceptual diagrams wherein a laser beam is incident on the side of a face, namely, the cheek, and a light receiving head assembly for leading the transmitted light into an optical fiber via a mixing optical system and then out of the oral cavity. FIG. 14 is a cross-sectional view taken along 14—14 of FIG. 13.

A human head 102 is fixed in relation to a bed 60. A laser beam passes through the cheek via the optical fiber 19 mounted on a rotary cylinder 61, which rotates with respect to the bed 60, and the optical system 31. The laser beam passes through the object to be measured such as the tooth 100 in the oral cavity and it is transmitted to the optical fiber 20 via the mixing optical system 32 which is fixed on an arm 62 mounted on the rotary cylinder 61 and which is placed on the opposite side of the optical system 31. This makes it possible to obtain tomographic images of a mandible bone and verify the state of stomatitis inside the cheek.

Regarding the wavelengths at which a laser beam is able to pass through a tooth, the blue beam of the argon laser having a wavelength of 488 nm was not transmitted through the tooth and image measurement could not be accomplished, whereas the green beam having a wavelength of 514.5 nm enabled the image measurement. Wavelengths longer than 514 nm exhibited good transmission through the tooth, enabling image measurement; however, the contrast of the images varied slightly between different wavelengths. Differences are observed in the absorption due to different hydroxyapatite in the wavelength range of 500 to 600 nm (preferably 500 to 560 nm) and the wavelength range of 830 to 1300 nm. This is significant in the image diagnosis for detecting a change, loss, or decrease in an enamel layer and/or a dentin layer or changes in the thicknesses of the two layers.

The images acquired at the different wavelengths may be used separately for performing diagnoses; however, it is also useful to create new images by performing addition/subtraction of images obtained at different wavelengths and to use the new processed images for diagnoses.

Thus, according to the present invention, the optical heterodyne method is used to implement the image measurement of a tooth or gum, enabling an image with a higher resolution than a conventional radiographic image to be obtained. Therefore, a tooth decay in its primary stage, for example, can be detected in a safe manner. The present invention is also useful for diagnosing periodontitis related to teeth and gums by measuring CT images.

In the present invention, high contrast images can be achieved by using light in the aforesaid green wavelength range.

It is also possible to acquire more effective and a greater volume of information on teeth and gums by measuring both an image obtained using the light in the green wavelength range and an image obtained using the light in the near infrared range.

What is claimed is:

1. An image measuring apparatus which is equipped with a light source for emitting light of a predetermined wavelength and which employs an optical heterodyne detection method to obtain an image of a tooth or gum by detecting the transmitted light in the transillumination mode.

2. The image measuring apparatus according to claim 1, wherein said light source emits light having at least one wavelength in a range of 500 nm or more to less than 600 nm.

3. The image measuring apparatus according to any one of claim 2, which is equipped with, in addition to said light source, a second light source that is used by being switched over from said light source and which emits light having at least one wavelength in a range of 600 nm or more to less than 1300 nm.

4. An image measuring apparatus according to claim 1, wherein said light source emits light having at least one wavelength in a range of 500 nm or more to less than 560 nm.

5. The image measuring apparatus according to claim 1, wherein said light source is an argon ion laser which emits light having a wavelength of 514.5 nm.

6. The image measuring apparatus according to claim 1, wherein said light source is the second harmonic of an Nd:YAG laser which emits light at the wavelength of 532 nm.

7. The image measuring apparatus according to claim 1, which is equipped with an incident optical fiber for transmitting light emitted from said light source into an oral cavity and a second optical fiber for receiving the light, which has passed through a tooth or gum, and out of the oral cavity.

8. An image measuring apparatus, comprising:
a first optical fiber transmitting light emitted from a light source at a predetermined wavelength; and
a second optical fiber for receiving the light which has passed through a tooth or gum and out of an oral cavity,
wherein either an emitting end of said first optical fiber or a receiving end of said second optical fiber is placed in the oral cavity and the other end is placed out of the oral cavity, and
wherein said image measuring apparatus employs an optical heterodyne detection method to obtain an image of the tooth or gum.

9. A method for measuring an image using at least one light source configured for emitting light of a predetermined wavelength, comprising the step of:
obtaining an image of a tooth or gum by detecting light emitted from the at least one light source in a transillumination mode using an optical heterodyne detection method.

10. A method for measuring an image using a first optical fiber, comprising the steps of:
emitting light from a light source at a predetermined wavelength;
receiving, using a second optical fiber, the light emitted from said light source which has passed through a tooth or gum and out of an oral cavity; and
obtaining an image of the tooth or gum by employing an optical heterodyne detection method,
wherein either an emitting end of said first optical fiber or a receiving end of said second optical fiber is placed in the oral cavity and the other end is placed out of the oral cavity.

11. An image measuring apparatus for obtaining the image of an oral cavity using an optical heterodyne method, said apparatus comprising:
an optical system receiving a laser beam emitted from a laser at a fixed wavelength;
a first optical coupler, coupled to the optical system, splitting the laser beam received by the optical system into a first beam and a second beam;
a frequency shifter, coupled to the first optical coupler, frequency shifting the first beam to provide a reference beam;
a second optical coupler, coupled to the first optical coupler and the frequency shifter, receiving the first beam which has been frequency shifted, receiving the second beam which has been transmitted and passed through the oral cavity, and mixing the first beam and the second beam, thereby generating an electrical signal; and
an optical detector, coupled to the second optical coupler, detecting the electrical signal, wherein a pathlength that the first beam travels is fixed.

* * * * *

Disclaimer

5,818,587—Balasigamani Devaraj; Masaki Kobayashi; Motohiro Takeda, all of Yamagata; Masashi Usa, Sendai; Hiroshi Ishihata, Sendai; Hiroshi Horiuchi, Sendai; Humio Inaba, Sendai, all of Japan. IMAGE MEASURING APPARATUS. Patent dated October 6, 1998. Disclaimer filed December 3, 2001, by assignee, Biophotonics Information Laboratories Ltd.

Hereby disclaims and dedicates to the public the term of Patent No. 5,818,587.
*(Official Gazette, May 7, 2002)*